United States Patent [19]

Poloyko et al.

[11] Patent Number: 5,339,801

[45] Date of Patent: Aug. 23, 1994

[54] SURGICAL RETRACTOR AND SURGICAL METHOD

[75] Inventors: Alexander Poloyko, Morton Grove, Ill.; Mark C. Goldberg, Boston, Mass.; Edward M. Goldberg, Glencoe, Ill.; Lev A. Melinyshyn, Buffalo Grove, Ill.; David E. Schucart, Homewood, Ill.

[73] Assignee: UreSil Corporation, Skokie, Ill.

[21] Appl. No.: 850,652

[22] Filed: Mar. 12, 1992

[51] Int. Cl.[5] .............................................. A61B 17/02
[52] U.S. Cl. .................................... 128/20; 128/17; 606/198
[58] Field of Search ............... 128/20, 3, 17; 606/190, 606/191, 197, 198, 205, 206, 208; 604/104, 106, 107–109

[56] References Cited

U.S. PATENT DOCUMENTS

| 430,849 | 6/1890 | Groth | 606/206 |
|---|---|---|---|
| 2,202,748 | 5/1940 | Solo | 128/20 |
| 4,655,219 | 4/1987 | Petruzzi | 128/6 X |
| 4,994,079 | 2/1991 | Genese et al. | 606/206 |
| 5,067,477 | 11/1991 | Santangelo | 128/20 |
| 5,098,440 | 3/1992 | Hillstead | 128/4 X |
| 5,152,279 | 10/1992 | Wilk | 128/20 X |
| 5,195,505 | 3/1993 | Josefsen | 128/20 |
| 5,199,419 | 5/1993 | Remiszewski et al. | 128/20 |

FOREIGN PATENT DOCUMENTS 0736949  5/1980  U.S.S.R. .................. 606/198

*Primary Examiner*—Richard J. Apley
*Assistant Examiner*—Donna L. Maraglio
*Attorney, Agent, or Firm*—Marshall, O'Toole, Gerstein, Murray & Borun

[57] ABSTRACT

A surgical retractor having a plurality of widenable and narrowable blades of substantial width, having tissue-contacting surfaces that are not significantly narrower, in a collapsed position, than a guide tube for guiding the retractor blades through a surgical access port to a surgical site during a minimally invasive surgical procedure. Each retractor blade includes a relatively large, preferably planar, tissue-contacting surface for displacing or repositioning internal body tissue, such as an internal organ, for temporary displacement away from the surgical site. After insertion through a surgical access port one or more of the retractor blades can be widened laterally to substantially space distal ends of the retractor blades apart for maximum contact against and over a substantial area of the tissue to be displaced during the surgical procedure. After completion of the operative procedure, the retractor blades can be narrowed by nesting the blades together and the retractor can be easily and safely withdrawn from the access port.

14 Claims, 2 Drawing Sheets

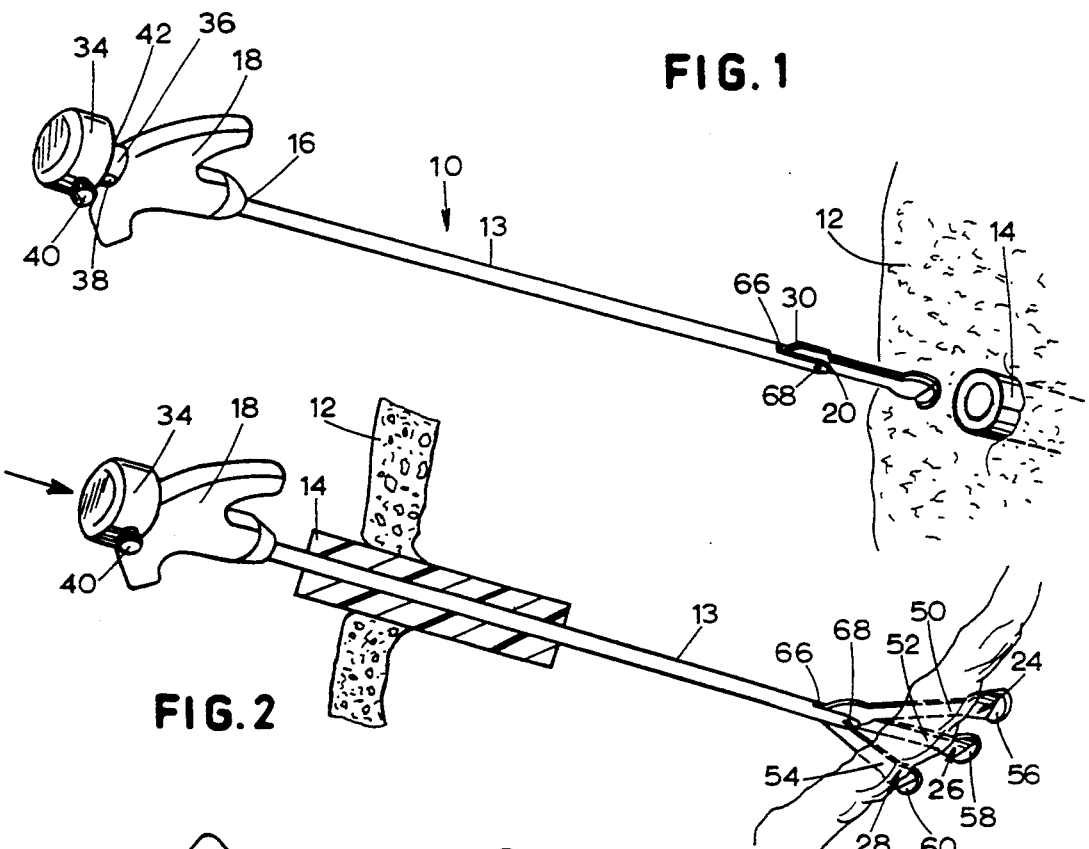
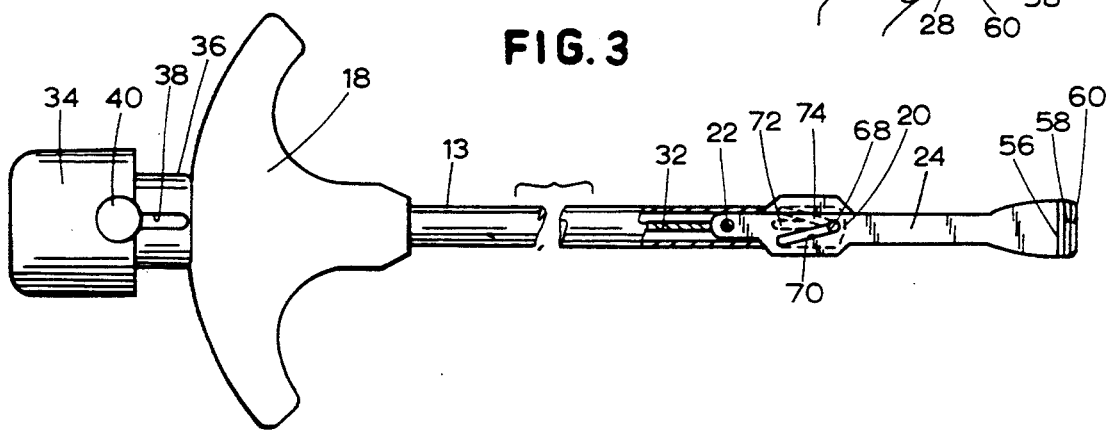
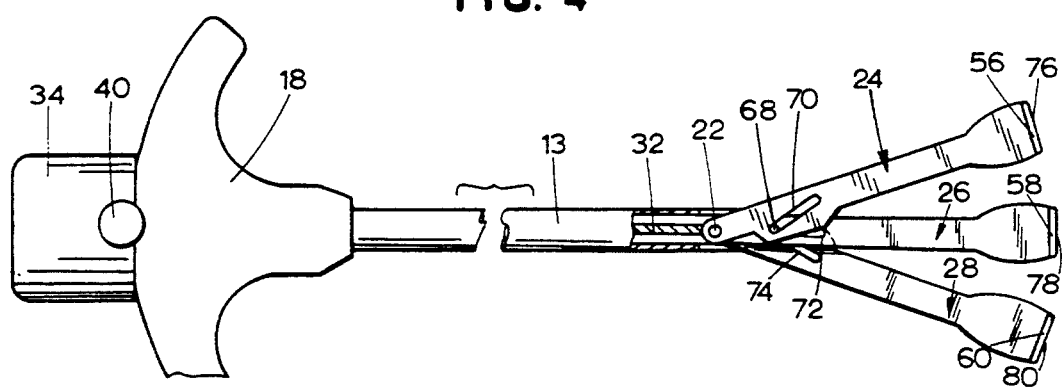

SURGICAL RETRACTOR AND SURGICAL METHOD

FIELD OF THE INVENTION

The present invention is directed to a surgical retractor that is capable of being narrowed for percutaneous insertion through a surgical access port and directed to a surgical site where it can be remotely widened and narrowed for moving internal tissue, such as a body organ, for improved observation of an unobstructed surgical field. More particularly, the present invention is directed to a widenable and narrowable laparoscopic surgical retractor that is sufficiently narrow for insertion through a surgical access port when a plurality of spreadable retractor blades are in a narrowed position, and that includes a linkage mechanism for spreading or narrowing the retractor blades at the surgical site.

BACKGROUND OF THE INVENTION AND PRIOR ART

The advantages of minimally invasive percutaneous, endoscopic surgical procedures are well documented.

The use of widenable and narrowable surgical devices, including dilation devices, blood vessel widening devices, grasping forceps and laparoscopic retractors are also known in the prior art as shown in the Groth U.S. Pat. No. 430,849; Graham U.S. Pat. No. 1,328,624; Suma U.S. Pat. No. 4,654,028; Taguchi et al. U.S. Pat. No. 4,909,789; Genese U.S. Pat. No. 4,994,079; and Santos U.S. Pat. No. 4,648,402.

The utilization of known prior art percutaneous, laparoscopic surgical retractors through an access port during minimally invasive surgery is difficult and requires precise, safe contact of tissue at a critical area for repositioning the tissue away from the surgical site, particularly when the retractor blades are formed from relatively thin material, such as metal wires. This disadvantage and others are overcome in the present invention by providing a surgical retractor which includes a plurality of spreadable and narrowable retractor blades that each includes a tissue-contacting planar surface that is substantially wider than prior art laparoscopic surgical retractor tissue-contacting surfaces, yet the retractor is capable of fitting through a conventional access port into a body cavity.

SUMMARY OF THE INVENTION

The present invention is directed to a laparoscopic surgical retractor having a plurality of spreadable and narrowable blades of substantial width, having main tissue-contacting surfaces that are not significantly narrower, in a narrowed position, than the inner diameter of a guide tube that guides the retractor blades through a surgical access port to a surgical site during a minimally invasive surgical procedure. Each retractor blade provides a relatively large, preferably planar, tissue-contacting surface for repositioning internal body tissue, such as an internal organ, for temporary displacement away from the surgical site. After insertion through a surgical access port, the retractor blades can be substantially spread laterally to space the distal ends of the retractor blades and position the blades for maximum contact against, and over a substantial area of, the tissue to be displaced during the surgical procedure.

Accordingly, one aspect of the present invention is to provide a new and improved remotely controllable surgical retractor for use in a minimally invasive surgical procedure capable of providing maximum contact against internal body tissue for temporary displacement of the tissue, thereby increasing access to a surgical site.

Another aspect of the present invention is to provide an improved laparoscopic surgical retractor that has a plurality of spreadable tissue-contacting blades that are remotely actuated into sliding angular relative movement to traverse a substantial area.

Still another aspect of the present invention is to provide a new and improved spreadable and narrowable laparoscopic surgical retractor having a plurality of spreadable, planar tissue-contacting blades wherein adjacent retractor blades overlie each other when in a narrowed position, and wherein remote actuation causes sliding angular movement of two retractor blades relative to a central, longitudinally aligned retractor blade to encompass a relatively large area.

BRIEF DESCRIPTION OF THE DRAWING

The above and other objects and advantages and novel features of the present invention will become apparent from the following detailed description of the preferred embodiment of the invention, taken in conjunction with the following figures of the drawings.

FIG. 1 is a perspective view of the surgical retractor of the present invention showing three retractor blades in a collapsed position for insertion into an access port installed at a trocar site during a minimally invasive surgical procedure;

FIG. 2 is a perspective view, similar to FIG. 1, showing the retractor inserted into the patient through an access port with the retractor blades in a widened orientation in contact with and displacing body tissue;

FIGS. 3 and 4 are enlarged, fragmentary partially elevated side views showing actuator linkages connected to the retractor blades for remotely narrowing (FIG. 3) and widening (FIG. 4) the retractor blades;

DETAILED DESCRIPTION OF THE PREFERRED EMBODIMENT

Figure 5:
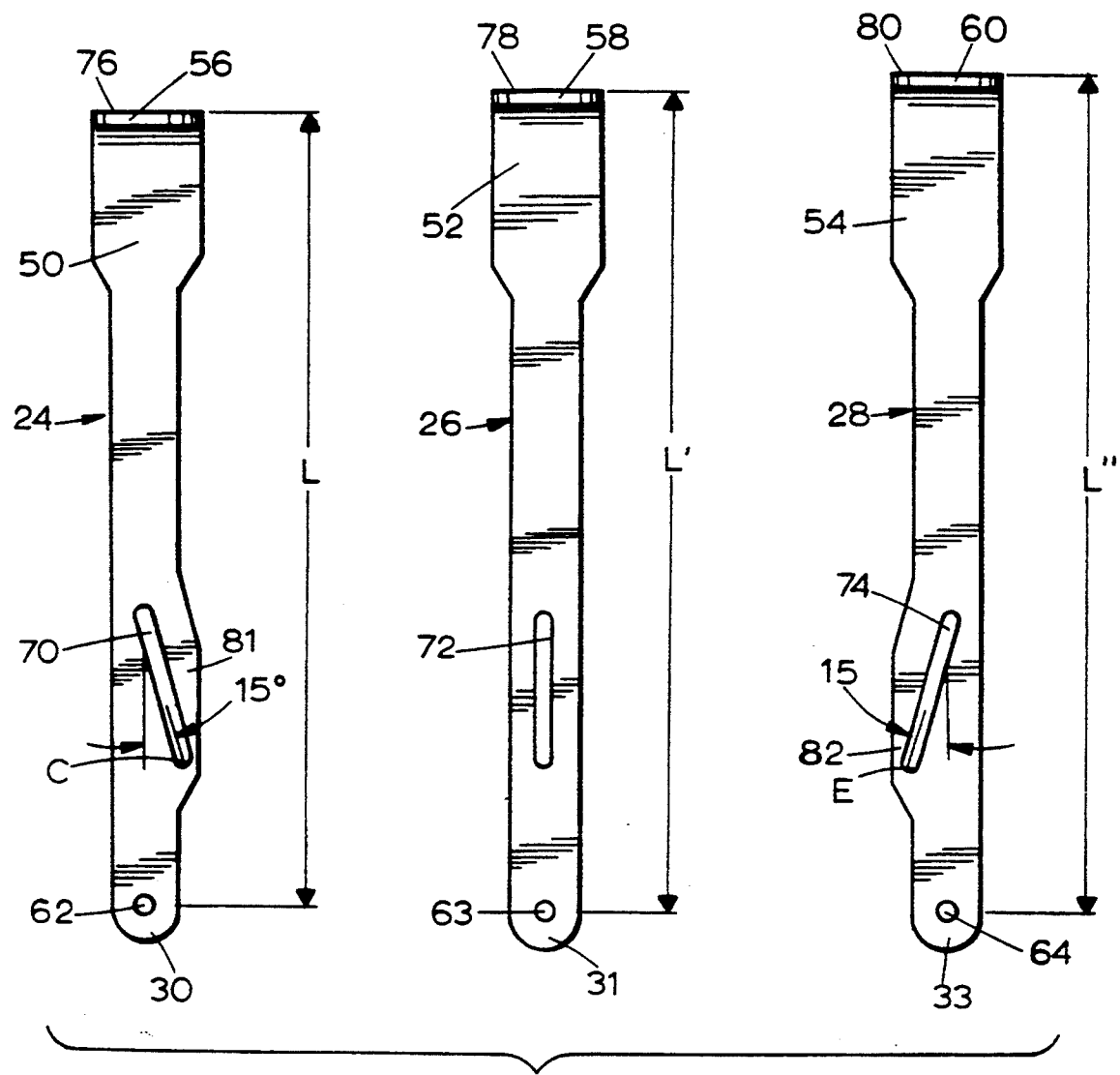
FIG. 5 is a top view of three elongate retractor blades removed from the retractor of FIG. 1 showing two of the blades with angled linkage-receiving slots for angular movement, upon actuation, relative to a third retractor blade that has a longitudinally disposed slot aligned with the longitudinal axis of the third retractor blade.

In accordance with the principles of the present invention, a widenable and narrowable laparoscopic surgical retractor 10 (FIGS. 1 and 2) is shown in a collapsed position in FIG. 1 for insertion into a patient 12 through a surgical access port or hollow tube 14 during a minimally invasive endoscopic surgical procedure. Access ports are conventional and include a one-way valve (not shown) for maintaining pressurization of a body cavity while permitting the introduction of surgical instruments. The retractor 10 is shown in a widened or operative position, within a patient, in FIG. 2. The retractor 10 includes an elongate guide member or hollow tube 13 secured at a proximal end 16 to a handle 18 and coupled at a distal end 20 through linkage pin 68 to a plurality of retractor blades 24, 26 and 28.

The retractor blades 24, 26 and 28 are held in alignment, in the collapsed or narrowed position, so that adjacent retractor blades overlie each other at aligned proximal ends 30, 31, and 33 (FIG. 5), respectively. The aligned retractor blades 24, 26 and 28 are rotatingly coupled to, and pivotally attached at a common pivot point adjacent to, a distal end 29 of an elongate actuator rod 32 by linkage pin 22 (FIGS. 3–5) so that axial movement of the elongate actuator rod 32 within the guide tube 13 causes longitudinal movement of the retractor blades 24, 26 and 28. The elongate actuator rod 32 is coupled at a proximal end to an actuator 34 for longitudinal movement of the retractor blades 24, 26 and 28 upon longitudinal movement of actuator 34. Actuator 34 is telescopically received over an axially extending portion 36 of the handle 18. The portion 36 includes a set screw-receiving slot 38 formed along its external surface in axial alignment with the guide tube 13, so that a set screw 40 threadedly journaled within an aperture 42 (FIG. 1) in the actuator 34 can be loosened for longitudinal movement of the actuator 34 over handle portion 36 toward and away from the retractor blades 24, 26 and 28, or the set screw 40 can be tightened within the slot 38 to lock the actuator 34 at any position along the slot 38 to lock the retractor blades 24, 26 and 28 at a desired degree of widening, such as the fully widened position shown in FIG. 4.

In accordance with an important feature of the present invention, each retractor blade 24, 26 and 28 includes a relatively wide main, tissue-contacting planar surface 50, 52 and 54, respectively. In a preferred embodiment, each retractor blade 24, 26 and 28 includes an integral planar surface 56, 58 and 60, respectively, extending transversely to the surfaces 50, 52 and 54 of the retractor blade 24, 26 and 28, respectively. When collapsed to the position shown in FIGS. 1 and 3, a centrally disposed retractor blade 26 is adjacent to and overlies lowermost retractor blade 28; and uppermost retractor blade 24 is adjacent to and overlies retractor blade 26. Each retractor blade 24, 26 and 28 is of slightly different length L, L', and L" wherein the length of each blade, relative to other blades, is as follows: L<L'<L" (FIG. 5), respectively, as measured from the central axes of a plurality of linkage pin-receiving apertures 62, 63 and 64 to a distal end 76, 78 and 80 of each blade 24, 26 and 28, respectively. The different lengths of each blade 24, 26 and 28 accommodate the aligned nesting of retractor blade portions 56, 58 and 60, as shown in FIG. 3. Each blade 24, 26, and 28 is fixedly coupled to the actuator rod 32 at proximal ends 30, 31 and 33 by the receipt in apertures 62, 63 and 64 of the linkage pin 22 secured to the rod 32 across a notch 65 (FIG. 6) formed in the distal end 29 of actuator rod 32 to accommodate the receipt and rotation of the ends 30, 31 and 33.

Figure 6:
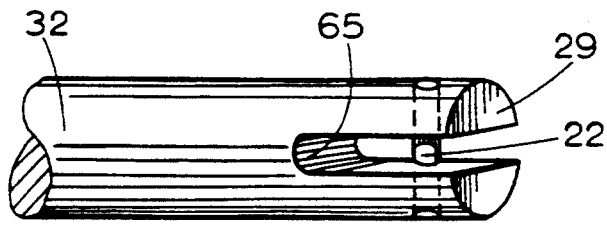
FIG. 6 is a fragmentary view showing an actuator rod and pin for securing the retractor blades (removed) to the actuator rod.

The guide tube 13 includes an axial notch 66 (FIG. 2) adapted to receive proximal end portions 30, 31 and 33 of each of the retractor blades 24, 26 and 28, respectively. The retractor blades 24, 26 and 28 are movably retained within the notch 66 by a linkage pin 68 received within a plurality of elongate slots 70, 72 and 74 disposed near the proximal end of each retractor blade 24, 26 and 28, respectively. In accordance with an important feature of the present invention, the elongate slot 72 is longitudinally aligned with and parallel to the longitudinal axis of the guide member 13 while the retractor blades 24 and 28 include elongate slots 70 and 74 angularly disposed to the longitudinal axis of the guide member 13, as best shown in FIG. 5. In this manner, when actuator 34 is axially moved toward the retractor blades 24, 26 and 28, thereby moving the actuator rod 32 to move the retractor blades 24, 26 and 28 axially outwardly, in a distal direction, linkage pin 68 slides along the slots 70, 72 and 74 in blades 24, 26 and 28. This movement causes sliding angular movement (i.e., relative rotation) of the retractor blades 24 and 28 in opposite directions, with respect to blade 26, to substantially space the distal ends 76 and 80 of retractor blades 24 and 28 from a distal end 78 of the retractor blade 26, (FIG. 4).

The elongate slot 72 (FIG. 5) is disposed along and in alignment with the longitudinal axis of retractor blade 26 so that axial movement of actuator rod 32 in a distal direction causes blade 26 to move longitudinally outwardly from the distal end 20 of the guide tube 13, in axial alignment with guide tube 13 as the linkage pin 68 slides along slot 72. Slots 70 and 74 in retractor blades 24 and 28, on the other hand, are angularly disposed with respect to the longitudinal axes of blades 24 and 28 so that axial movement of actuator rod 32 in a distal direction causes blades 24 and 28 to move longitudinally and outwardly from the distal end 20 of guide tube 13.

The retractor blades 24 and 28 include integral enlarged portions 81 and 82 extending laterally outwardly from the blades 24 and 28 adjacent to slots 70 and 74, respectively, to accommodate the placement of the proximal end C of angled slot 70 and proximal end E of angled slot 74 within the blades 24 and 28. The slots 70, 72 and 74 have the same longitudinal extension measured along the longitudinal axes of the blades 24, 26 and 28. The slots 70 and 74 are disposed at slot angles of from about 5° to about 25°, preferably 10° to about 20°, for example about 15°, from the longitudinal axes of the blades 24 and 28, respectively.

Numerous modifications and alternative embodiments of the present invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A surgical retractor comprising:
   an elongate guide member having proximal and distal ends, a longitudinal axis, and a pin adjacent to the distal end;
   an actuator in proximity to the proximal end of the guide member;
   a rod attached to the actuator, axially movable with respect to the guide member upon actuation of the actuator, and having a distal end in proximity to the pin; and
   at least two retractor blades pivotally attached to the rod at a common pivot point adjacent to the distal end of the rod and spaced from the pin adjacent to the distal end of the guide member, each blade having elongated slot means engaging the pin for affording relative rotation of the retractor blades with respect to each other in response to axial movement of the rod.

2. A surgical retractor comprising:
   an elongate guide member having proximal and distal ends, a longitudinal axis, and a pin adjacent to the distal end;

an actuator in proximity to the proximal end of the guide member;

a rod attached to the actuator, axially movable with respect to the guide member upon actuation of the actuator, and having a distal end in proximity to the pin; and at least two retractor blades pivotally attached to the rod at a common pivot point adjacent to the distal end of the rod and spaced from the pin adjacent to the distal end of the guide member, each blade having elongated slot means engaging the pin for rotating one of the blades in one direction with respect to the guide member and rotating another of the blades in another direction with respect to the guide member in response to axial movement of the rod.

3. A surgical retractor as defined in claim 2, wherein the blades each include a main planar surface portion and an integral surface portion angularly disposed with respect to the main portion.

4. A surgical retractor as defined in claim 2 including three retractor blades pivotally attached to the rod at a common pivot point adjacent to the distal end of the rod.

5. A surgical retractor as defined in claim 2, wherein the retractor blades each include a main planar surface portion and an integral surface portion angularly disposed with respect to the main portion.

6. A surgical retractor as defined in claim 5, wherein the integral portion of each retractor blade is substantially planar.

7. A surgical retractor as defined in claim 6, wherein the main portion of each retractor blade extends in a plane transverse to the plane of the integral portion.

8. A surgical retractor as defined in claim 7, wherein the integral portion is disposed at a distal end of the main portion of each retractor blade.

9. A surgical retractor as defined in claim 2 including three retractor blades.

10. A surgical retractor as defined in claim 9, wherein the slot means of each retractor blade includes a slot, and the slot in one of the retractor blades is disposed in longitudinal alignment with the longitudinal axis of the guide member and wherein the slots in the remaining retractor blades are angularly disposed with respect to the longitudinal axis of the guide member, so that axial movement of the rod retains the one retractor blade in longitudinal alignment with the guide member and causes the remaining retractor blades to spread outwardly at their distal ends.

11. A surgical retractor as defined in claim 10, wherein each slot in each remaining retractor blade is disposed at an angle of from about 5° to about 25° from the longitudinal axis of each remaining retractor blade.

12. A surgical retractor as defined in claim 11, wherein each slot in each remaining retractor blade is disposed at an angle of from about 10° to about 20° from the longitudinal axis of each remaining retractor blade.

13. A surgical retractor as defined in claim 12, wherein each slot in each remaining retractor blade is disposed at an angle of from about 10° to about 15° from the longitudinal axis of each remaining retractor blade.

14. A surgical retractor comprising:

a hollow tube having proximal and distal ends and a longitudinal axis;

an actuator in proximity to the proximal end of the hollow tube;

a notch adjacent the distal end of the hollow tube;

a rod within the hollow tube, one end of the rod being connected to the actuator for selective movement of the rod along the tube axis upon actuation of the actuator;

a linkage pin adjacent the end of the rod opposite to the actuator, mounted on the rod for movement with the rod along the tube axis;

at least three elongate retractor blades pivotally mounted to the linkage pin with the linkage pin serving as a common pivot pint, each of the retractor blades having a longitudinal blade axis passing through the linkage pin and a planar blade portion extending along the blade axis between the linkage pin and a nesting end that in turn extends out of the plane of the planar blade portion;

an elongate slot in an upper blade of the retractor blades extending to one side of the retractor blade at about a 10°-20° angle with respect to the blade axis of the upper blade;

a second elongate slot in a lower blade of the retractor blades extending to the opposite side of the retractor blade at about a 10°-20° angle with respect to the blade axis of the lower blade;

a third elongate slot in an intermediate blade of the retractor blades extending along the blade axis of the intermediate blade; and a second linkage pin, spaced from the first linkage pin, extending between the notch adjacent the distal end of the hollow tube and through the slots in the retractor blades so that, when the rod is moved along the tube axis, the upper retractor blade rotates in one direction with respect to the hollow tube, the lower retractor blade rotates in the opposite direction with respect to the hollow tube, and the intermediate retractor blade does not rotate with respect to the hollow tube.

* * * * *